United States Patent [19]

Motai et al.

[11] Patent Number: 4,684,527
[45] Date of Patent: Aug. 4, 1987

[54] PROCESS FOR PRODUCING SEASONING

[75] Inventors: Hiroshi Motai; Yaichi Fukushima, both of Noda; Takashi Ishiyama, Saitama, all of Japan

[73] Assignee: Kikkoman Corporation, Noda, Japan

[21] Appl. No.: 846,631

[22] Filed: Apr. 1, 1986

[51] Int. Cl.$^4$ .......................... A23L 1/20; A23L 1/221
[52] U.S. Cl. ....................................... 426/46; 426/52; 426/650
[58] Field of Search ..................... 426/656, 46, 52, 60, 426/63, 634, 650

[56] References Cited

U.S. PATENT DOCUMENTS

| | | | |
|---|---|---|---|
| 3,852,479 | 12/1974 | Yokotsuka et al. | 426/46 |
| 4,016,293 | 4/1977 | Coughlin et al. | 426/42 |
| 4,587,127 | 5/1986 | Akao et al. | 426/52 |

FOREIGN PATENT DOCUMENTS 57-18858  4/1982  Japan .
57-48946 10/1982  Japan .
57-55388 11/1982  Japan .

Primary Examiner—Raymond N. Jones
Assistant Examiner—Marianne M. Cintins
Attorney, Agent, or Firm—Banner, Birch, McKie and Beckett

[57] ABSTRACT

A process for producing a seasoning is disclosed wherein a hydrolyzate of soy sauce koji prepared from soy sauce raw materials, in a liquid state at a pH of 2.5 to 8.0, is contacted with an immobilized peptidase and/or immobilized glutaminase in the presence of sodium chloride to react therewith.

3 Claims, No Drawings

PROCESS FOR PRODUCING SEASONING

BACKGROUND OF THE INVENTION

1. Field of the Invention

This invention relates to a process for producing a seasoning of excellent flavor and taste.

2. Description of the Prior Art

There has already been known a method of obtaining a seasoning of a high glutamic acid content which comprises, in the hydrolysis of proteinous raw materials by enzymes, subjecting the raw materials to the action of protease containing substantially no peptidase, and then subjecting the resulting product to the action of peptidase and glutaminase in the absence of sodium chloride (see, for example, Japanese Patent Publication No. 48946/82).

Prior art methods of preparing a seasoning by the hydrolysis of proteinous raw materials using enzyme preparations, including the above-mentioned method of preparing a seasoning disclosed in Japanese Patent Publication No. 48946/82, still have defects in that the efficiency of contact and reaction between the substrate and enzyme is low even when reaction conditions such as pH and temperature are properly adjusted and further the enzyme used in the reaction cannot be employed respectively, resulting in high production cost.

Accordingly, there has been eagerly awaited in the industry the improvement of a process which gives an enhanced contact efficiency between protein substrate and enzyme and can thus produce a seasoning in good efficiency.

SUMMARY OF THE INVENTION

The present inventors have made extensive studies on the reaction conditions between substrates and enzymes in preparing a seasoning. As a result, it has been found that a seasoning of high amino acid content and markedly excellent flavor and taste can be obtained in good efficiency by first preparing soy sauce koji beforehand from soy sauce raw materials according to conventional method of soy sauce production, hydrolyzing the koji, and then contacting the resulting hydrolyzate, in a liquid state at a pH of 2.5 to 8.0, with an immobilized peptidase and/or immobilized glutaminase in the presence of sodium chloride to react therewith. This invention has been accomplished on the basis of above finding.

Thus, this invention relates to a process for producing a seasoning which comprises contacting a hydrolyzate of soy sauce koji prepared from soy sauce raw materials, in a liquid state at a pH of 2.5 to 8.0, with an immobilized peptidase and/or immobilized glutaminase in the presence of sodium chloride to react therewith.

DETAILED DESCRIPTION OF THE INVENTION

The raw materials for the soy sauce production used in this invention are those usually used in the production of soy sauce, that is to say, proteinous materials admixed with starchy materials. As examples of suitable proteinous materials, there may be listed defatted soybean, whole soybean, wheat gluten, corn gluten, purified soybean gluten, separated soluble protein, fishes and shellfishes, meats, and yeast extracts. Examples of suitable starchy materials include wheat, barley and corn.

These raw materials are subjected to customary raw material treatment such as softening of the tissue, denaturation of proteins, conversion of starch into α-form, and sterilization.

These soy sauce raw materials are inoculated with yellow koji-molds such as *Aspergillus oryzae* and *Aspergillus soyae*, which are common koji-molds for soy sauce production, and then made into koji in a customary manner for about 25 to 100 hours at 25° to 40° C. by conventional methods such as koji-tray method and koji-making method under aeration to give soy sauce koji.

The hydrolysis of the soy sauce koji is carried out by adding a sodium cloride aqueous solution to the koji and hydrolyzing it at about 30° to 60° C. while gently stirring the mixture just to keep the substrates from settling. The sodium chloride concentration is kept at 1 to 20% (W/V), preferably 5 to 12% (W/V), during the hydrolysis step. The hydrolysis is carried out preferably under sterile conditions or at a relatively elevated temperature such as 40° to 90° C., preferably 45° to 65° C., for at least about 10 hours, preferably 24 to 120 hours.

The reaction mixture obtained by the hydrolysis of soy sauce koji as described above is adjusted, unless its original pH lies in the range of 2.5 to 8.0, to a pH of 2.5 to 8.0, preferably 4.0 to 6.5, by addition of suitable alkali or acid. When the hydrolyzate obtained as described above is a liquid containing no or substantially no residue of hydrolysis (solids), it is used as such; otherwise the hydrolyzate is subjected to solid-liquid separation by conventional means such as pressing, filtration, and centrifugation before and/or after adjusting pH to 2.5 to 8.0 with an alkali or an acid as mentioned above to obtain a substrate in liquid form.

The peptidase and/or glutaminase used in this invention is of any origin so long as they can exert their enzymatic activity at a pH of 2.5 to 8.0.

Preferable examples of peptidase to be used include, in the case of aminopeptidase, those of the genus Aspergiillus, Streptomyces, Lactobacillus, and Pediococcus origin and, in the case of carboxypeptidase, those of the genus Aspergillus and Penicillium origin.

Preferable example of glutaminase to be used include those originated from such microorganisms as the genus Saccharomyces, Aspergillus, and Echerichia.

As examples of such peptidase and glutaminase of microbial origin, mention may be made of a culture liquor containing peptidase and/or glutaminase obtained by inoculating and cultivating the cells of these microorganisms in a medium by conventional methods, cells separated from said culture liquor or disintegrated products thereof, a crude enzyme solution obtained from said culture liquor by filtration or centrifugation, or purified enzyme obtained by purifying it in a conventional manner.

The immobilized peptidase and immobilized glutaminase used in this invention can be obtained by any conventional methods of immoblization. That is, in the case of above-mentioned crude enzyme solution or purified enzyme, there may be mentioned as examples of preferred methods of immobilization, as to the ionic bond method a method which comprises bonding said enzyme to ion exchangers such as DEAE Sephadex, QAE Sephadex, Dowex 1X1, and Amberlite IRA-45 and then subjecting it, if necessary, to crosslinking with glutaraldehyde; as to the adsorption method one which comprises allowing said enzyme to be adsorbed onto adsorbents such as active carbon, silica gel, and alumina, and then subjecting it, if necessary, to crosslinking with glutaraldehyde; as to the covalent bond method one which comprises mixing said enzyme with, for example, a polysaccharide activated with cyanogen bromide or a polysaccharide to which an epoxy group has been introduced by using a bisoxysilane compound; as to the entrapping method one which comprises mixing said enzyme with a gel base of alginic acid salt or a liquid mixture of alginic acid salt and silica sol and bringing the resulting mixture in contact with a gelling agent, or mixing the enzyme with a gel base of a solution of carrageenan or algae which has been formed by heating them with water, and then cooling the resulting mixture.

In the case of above-mentioned culture liquor, separated cells, or disintegrated cells, particularly preferable methods of immobilization include those of entrapping which comprise mixing them with a gel base of alginic acid salt or a liquid mixture of alginic acid salt and silica sol and bringing the resulting mixture in contact with a gelling agent, or mixing them with a gel base of a solution of carrageenan or algae, which has been formed by heating them with water, and then cooling the resulting mixture.

The immobilized peptidase and/or immobilized glutaminase obtained by the procedures described above are placed in an hydrolysis vessel, such as a packed tower, stirring tank, fluidized bed contactor, bubbling column, and film reactor, and then the hydrolyzate of soy sauce koji in liquid state at a pH of 2.5 to 8.0 mentioned above, namely a liquid substrate, is introduced to the vessel and allowed to contact and react, continuously or intermittently, with the immobilized peptinase and/or immobilized glutaminase in the presence of sodium chloride to give a seasoning of excellent flavor and taste.

In the above-mentioned contact and reaction of the liquid substrate (hydrolyzate) of a pH of 2.5 to 8.0 with immobilized peptidase and/or immobilized glutaminase, the concentration of sodium chloride is usually about 3 to 20% (W/V), preferably about 8 to 17% (W/V), the contact temperature is about 20° to 60° C., preferably 25° to 50° C., and the contact time is preferably about 5 minutes to 24 hours, preferably 30 minutes to 10 hours.

When both of immobilized peptidase and immobilized glutaminase are used in the above-mentioned reaction of the liquid substrate (hydrolyzate) with immobilized peptidase and/or immobilized glutaminase, it is preferable to bring the substrate into contact first with immobilized peptidase and then with immobilized glutaminase for increasing the enzyme reaction efficiency of the substrate.

Although the liquid seasoning obtained after contact with immobilized peptidase and/or immobilized glutaminase as described above can be used as such or optionally after filtration, a liquid seasoning with more excellent flavor and taste can be prepared, if necessary, by further ripening after usual enzyme fermentation or suitable processing followed by usual treatments such as filtration, pasteurization, and sediment separation.

As described above, according to this invention, it is possible to prepare efficiently a seasoning of high amino acid content and excellent flavor and taste. This invention is, therefore, of great significance from the industrial point of view.

This invention is further illustrated below in detail with reference to Examples, but the invention is not limited thereto.

EXAMPLE 1

One liter of a liquid medium (pH 6.0) containing 0.5% (W/V) of defatted soybean meal and 2.0% (W/V) of wheat bran was placed in a 5 l flask and sterilized in a conventional manner. *Aspergillus awamori* ATCC 20793 which had been pre-cultured beforehand in a medium of the above-mentioned composition was inoculated to said sterilized medium and subjected to shaken culture at 30° C. for 48 hours. The culture liquor thus obtained was centrifuged in a conventional manner to remove bacterial cells. The resulting liquid was adjusted to pH 5.2 with an 1N sodium hydroxide aqueous solution, and then 3 times its amount (V/V) of cold ethanol was added thereto to cause precipitation. After being allowed to stand over-night, the mixture obtained above was centrifuged to obtain a precipitate. It was then dried under vacuum to give a carboxypeptidase preparation (34 U/mg).

Five grams of the carboxypeptidase preparation obtained as described above was dissolved in an acetate buffer solution (pH 6.0) and then adsorbed onto DEAE Toyopearl 650 (a trade name, mfd. by Toyo Soda Mfg. Co., Ltd.). Then, 2% (W/V) glutaraldehyde solution was added thereto and allowed to react at 4° C. for 16 hours to obtain an immobilized carboxypeptidase.

On the other hand, 1 l of a liquid medium (pH 5.5) containing 4% (W/V) of glucose, 6% (W/V) of corn steep liquor, 0.1% (W/V) of potassium primary phosphate, and 0.1% (W/V) of magnesium sulfate was placed in a 3 l jar fermenter and sterilized in a conventional manner. To the sterilized medium was added 50 ml of a seed culture fluid obtained by inoculating beforehand *Cryptococcus albidus* ATCC 20293, a glutaminase-producing yeast, to a medium of the above-mentioned composition and subjecting it to shaken culture at 25° C. for 42 hours. It was then cultivated under aerobic conditions at 25° C. for 30 hours with an air flow rate of 1 l/minute and a stirring velocity of 300 r.p.m. After completion of the cultivation, the resulting culture liquor was centrifuged and the separated cells were washed twice with water. The cultured cells thus obtained were thoroughly mixed with 90 g of 2% (W/V) sodium alginate, and the mixture was added dropwise by means of a syringe to a 5% (W/V) calcium chloride solution to obtain spherical gel granules of cells containing immobilized glutaminase.

Then, a mash for koikuchi soy sauce which had been obtained by decomposing normal soy sauce koji [raw material composition: defatted soybean:wheat=50:50 (W/W)] at 30° C. for 1 month was pressed in a customary manner to give a liquid mash [pH 5.5, NaCl 16.5% (W/V), T.N. 1.75% (W/V)]. The liquid mash was then passed continuously through a column (inner diameter: 1.5 cm) provided with a jacket, packed with 10 g of above-mentioned immobilized carboxypeptidase, and kept at a temperature of 33° C., at a rate of 0.05 ml (liquid mash)/minute. Then, the liquid thus obtained was passed continuously through a column (inner diameter: 1.5 cm) provided with a jacket, packed with 10 g of above-mentioned immobilized glutaminase-containing cells and kept at 33° C., at a rate of 0.05 ml (liquid)/minute. Thus, a seasoning of high glutamic acid content and excellent flavor and taste as shown in Table 1 was obtained continuously.

TABLE 1

|  | before passing through column | After passing through column |
|---|---|---|
| T.N.* (%(W/V)) | 1.75 | 1.75 |
| Total amino acids (mg/ml) | 58.6 | 71.8 |
| Glutamic acid (mg/ml) | 8.8 | 14.5 |

*T.N.: Total nitrogen

EXAMPLE 2

One liter of a liquid medium (pH 6.0) containing 0.5 % (W/V) of defatted soybean meal and 2% (W/V) of wheat bran was placed in a 5 l flask and sterilized in a conventional manner. *Asperqillus oryzae* 460 FERM BP-983 which had been pre-cultured beforehand in a medium of the above-mentioned composition was inoculated to said sterilized medium, and subjected to shaken culture at 30° C. for 48 hours. The culture liquor thus obtained was centrifuged in a conventional manner to remove mycelium. The resulting liquid was subjected to ammonium sulfate fractionation and then purified by the use of DEAE-cellulose (mfd. by Brown Co., U.S.A.) to obtain a leucine aminopeptidase preparation.

Five grams of the leucine aminopeptidase preparation obtained above was dissolved in a phosphate buffer solution (pH 7.0), and then adsorbed onto 100 g of moistened DEAE-Sephadex A-25 (mfd. by Pharmacia Co., Sweden). Then, 2% (W/V) glutaraldehyde solution was added thereto and allowed to react at 4° C. for 16 hours to obtain an immobilized leucine aminopeptidase.

On the other hand, 1 l of a liquid medium (pH 5.5) containing 4% (W/V) of glucose, 6 % (W/V) of corn steep liquor, 0.1% (W/V) of potassium primary phosphate, and 0.1% (W/V) of magnesium sulfate was placed in a 3 l jar fermenter and sterilized in a conventional manner. To the sterilized medium was added 50 ml of a seed culture fluid obtained by inoculating beforehand *Cryptococcus albidus* ATCC 20293, a glutaminase-producing yeast, to a medium of the above-mentioned composition and subjecting it to shaken culture at 25° C. for 42 hours. It was then cultivated under aerobic conditions at 25° C. for 30 hours with an air flow rate of 1 l/minute and a stirring velocity of 300 r.p.m. After completion of the cultivation, the resulting culture liquor was centrifuged and the separated cells were washed twice with water. The cells thus obtained were suspended in an acetate buffer solution (pH 6.0) with ice cooling, then disintegrated by means of an ultrasonic disintegrator (mfd. by Nippon Seiki Seisakusho K.K.) at 20 KC, and centrifuged to obtain a solution containing glutaminase.

The solution containing glutaminase obtained above was adsorbed onto QAE-Sephadex (mfd. by Pharmacia Co., Sweden). Then, 2% (W/V) glutaraldehyde solution was added thereto and allowed to react at 4° C. for 16 hours to obtain an immobilized glutaaminase.

Then, a mash for koiguchi soy sauce which had been obtained by decomposing normal soy sauce [raw material composition : defatted soybean: wheat =50:50 (W/W)] at 30° C. for 1 month was pressed in a customary manner to give a liquid mash [pH 6.0, NaCl 16.5% (W/V), T.N. 1.75% (W/V)]. The liquid mash was then passed continuously through a column (inner diameter: 1.5 cm) provided with a jacket, packed with 10 g of above-mentioned immobilized leucine aminopeptidase and kept at a temperature of 35° C., at a rate of 0.05 ml (liquid mash)/minute. Then, the liquid thus obtained was continuously passed through a column provided with a jacket, packed with 10 g of the above-mentioned immobilized glutaminase and kept at 35° C., at a rate of 0.05 ml (liquid)/minute. Thus, a seasoning of high glutamic acid content and excellent flavor and taste as shown in Table 2 was obtained continuously.

TABLE 2

|  | before passed through column | After passed through column |
|---|---|---|
| T.N. (%(W/V)) | 1.75 | 1.75 |
| Total amino acids (mg/ml) | 58.6 | 70.5 |
| Glutamic acid (mg/ml) | 8.8 | 10.8 |

What is claimed is:

1. A process for producing a seasoning which comprises contacting at a temperature of 20° to 60° C. and for a time of 5 minutes to 24 hours a hydrolyzate of soy sauce koji prepared from soy sauce raw materials, in a liquid state at a pH of 2.5 to 8.0, with an immobilized glutaminase or with an immobilized peptidase and immobilized glutaminase in the presence of sodium chloride at a concentration of 3 to 20% (W/V).

2. A process according to claim 1, wherein the contacting of the hydrolyzate with the immobilized peptidase and immobilized glutaminase is carried out by contacting the hydrolyzate first with the immobilized peptidase and then with the immobilized glutaminase.

3. A process according to claim 1, wherein the immobilized peptidase and immobilizing glutaminase are each placed in a packed tower, stirred tank, fluidized bed reactor, bubbling column or film reactor.

* * * * *